United States Patent
Patil et al.

(10) Patent No.: US 9,688,677 B1
(45) Date of Patent: Jun. 27, 2017

(54) PROCESS FOR PREPARATION OF SODIUM (2S, 5R)-6-(BENZYLOXY)-7-OXO-1,6-DIAZABICYCLO[3.2.1]OCTANE-2-CARBOXYLATE

(71) Applicant: WOCKHARDT LIMITED, Aurangabad, Maharashtra (IN)

(72) Inventors: Vijaykumar Jagdishwar Patil, Solapur (IN); Ravikumar Tadiparthi, Aurangabad (IN); Satish Birajdar, Taluka Ausa (IN); Mohammad Usman Shaikh, Shrirampur (IN); Mahesh Vithalbhai Patel, Aurangabad (IN)

(73) Assignee: WOCKHARDT LIMITED, Chikalthana, Aurangabad (IN)

( * ) Notice: Subject to any disclaimer, the term of this patent is extended or adjusted under 35 U.S.C. 154(b) by 0 days.

(21) Appl. No.: 15/129,971

(22) PCT Filed: Mar. 12, 2015

(86) PCT No.: PCT/IB2015/051797
§ 371 (c)(1),
(2) Date: Sep. 28, 2016

(87) PCT Pub. No.: WO2015/150941
PCT Pub. Date: Oct. 8, 2015

(30) Foreign Application Priority Data

Mar. 29, 2014 (IN) .......................... 1192/MUM/2014

(51) Int. Cl.
*C07D 401/04* (2006.01)
*A61K 31/407* (2006.01)
*C07D 471/08* (2006.01)
*C07D 211/60* (2006.01)

(52) U.S. Cl.
CPC .......... *C07D 471/08* (2013.01); *C07D 211/60* (2013.01)

(58) Field of Classification Search
CPC ...................................................... C07D 401/04
USPC .......................................... 546/121; 514/300
See application file for complete search history.

(56) References Cited

FOREIGN PATENT DOCUMENTS

| EP | 2 657 234 A1 | 10/2013 |
| WO | 2013/038330 A1 | 3/2013 |
| WO | 2013/180197 A1 | 12/2013 |
| WO | 2014/135929 S1 | 9/2014 |

*Primary Examiner* — Niloofar Rahmani
(74) *Attorney, Agent, or Firm* — Bio Intellectual Property Services LLC (Bio IPS); O. (Sam) Zaghmout

(57) ABSTRACT

A process for preparation of a compound of Formula (I) is disclosed.

Formula (I)

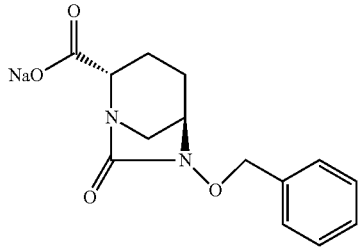

11 Claims, No Drawings

PROCESS FOR PREPARATION OF SODIUM (2S, 5R)-6-(BENZYLOXY)-7-OXO-1,6-DIAZABICYCLO[3.2.1]OCTANE-2-CARBOXYLATE

RELATED PATENT APPLICATION

This application claims priority to Indian Patent Application No. 1192/MUM/2014 filed on Mar. 29, 2014, the disclosures of which are incorporated herein by reference in its entirety as if fully rewritten herein.

FIELD OF THE INVENTION

The invention relates to a process for preparation of sodium (2S, 5R)-6-(benzyloxy)-7-oxo-1,6-diazabicyclo[3.2.1]octane-2-carboxylate.

BACKGROUND OF THE INVENTION

A compound of Formula (I), chemically known as sodium (2S, 5R)-6-(benzyloxy)-7-oxo-1,6-diazabicyclo[3.2.1]octane-2-carboxylate, can be used as an intermediate in the synthesis of several antibacterial compounds and is disclosed in PCT International Patent Application No. PCT/IB2013/059264. The present invention discloses a process for preparation of a compound of Formula (I).

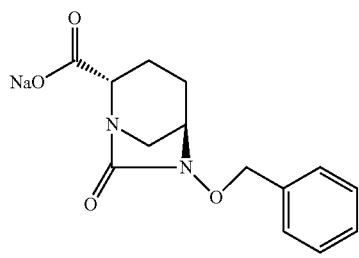

Formula (I)

SUMMARY OF THE INVENTION

In one general aspect, there is provided a process for preparation of a compound of Formula (I), said process comprising:

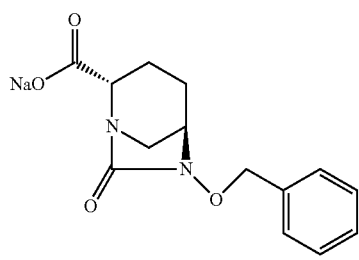

Formula (I)

(a) converting a compound of Formula (II) to a compound of Formula (IV);

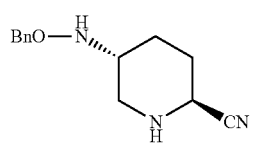

Formula (II)

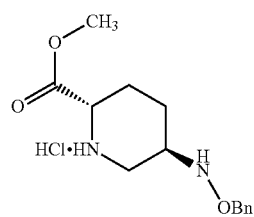

Formula (IV)

(b) cyclizing a compound of Formula (IV) to obtain a compound of Formula (V); and

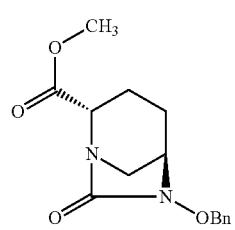

Formula (V)

(c) converting a compound of Formula (V) to a compound of Formula (I).

In another general aspect, there is provided a process for preparation of a compound of Formula (I), said process comprising:

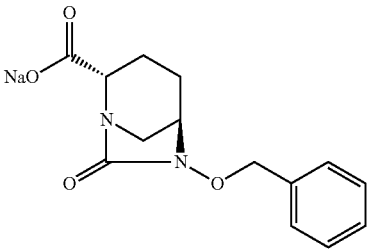

Formula (I)

(a) hydrolysis of a compound of Formula (II) to obtain a compound of Formula (III);

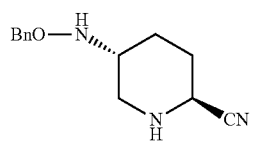

Formula (II)

Formula (III)

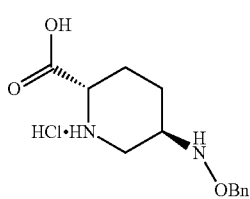

(b) reacting a compound of Formula (III) with di-tert-butyldicarbonate to obtain a compound of Formula (VI);

Formula (VI)

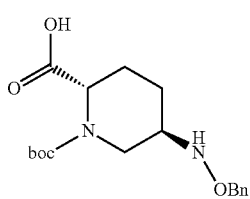

(c) reacting a compound of Formula (VI) with 4-methoxy-benzyl alcohol to obtain a compound of Formula (VII);

Formula (VII)

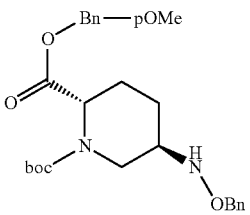

(d) hydrolysis of a compound of Formula (VII) to obtain a compound of Formula (VIII);

Formula (VIII)

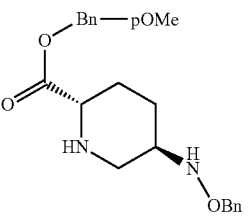

(e) cyclizing a compound of Formula (VIII) to obtain a compound of Formula (IX); and Formula (IX)

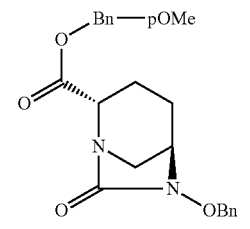

(f) converting a compound of Formula (IX) to a compound of Formula (I).

The details of one or more embodiments of the inventions are set forth in the description below. Other features, objects and advantages of the inventions will be apparent from the following description including claims.

DETAILED DESCRIPTION OF THE INVENTION

Reference will now be made to the exemplary embodiments, and specific language will be used herein to describe the same. It should nevertheless be understood that no limitation of the scope of the invention is thereby intended. Alterations and further modifications of the inventive features illustrated herein, which would occur to one skilled in the relevant art and having possession of this disclosure, are to be considered within the scope of the invention. It must be noted that, as used in this specification and the appended claims, the singular forms "a", "an", and "the" include plural referents unless the content clearly dictates otherwise. All references including patents, patent applications, and literature cited in the specification are expressly incorporated herein by reference in their entirety.

The term "OBn" as used herein refers to benzyloxy.

The term "EDC" as used herein refers to 1-ethyl-3-(3-dimethylaminopropyl)carbodiimide.

The term "HOBt" as used herein refers to 1-hydroxybenzotriazole.

The term "DMAP" as used herein refers to 4-dimethylaminopyridine.

The term "Boc anhydride" as used herein refers to di-tert-butyldicarbonate.

The term "Boc" as used herein refers to N-tert-butyloxycarbonyl.

The term "Bn-pOMe" as used herein refers to 4-methoxy benzyl.

In one general aspect, there is provided a process for preparation of a compound of Formula (I), said process comprising:

Formula (I)

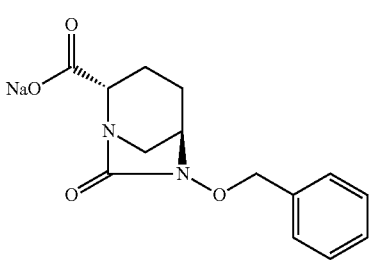

(a) converting a compound of Formula (II) to a compound of Formula (IV);

Formula (II)

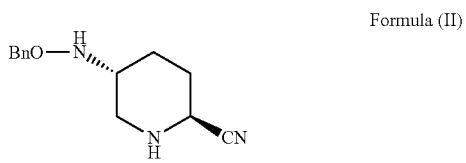

-continued

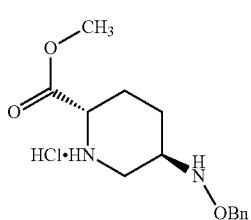

Formula (IV)

(b) cyclizing a compound of Formula (IV) to obtain a compound of Formula (V); and

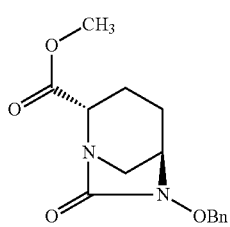

Formula (V)

(c) converting a compound of Formula (V) to a compound of Formula (I).

In some embodiments, compound of Formula (I) is prepared by using a general procedure described in Scheme 1. Typically, sodium (2S, 5R)-6-(benzyloxy)-7-oxo-1,6-diazabicyclo [3.2.1]octane-2-carboxylate (I) is prepared from (2S, 5R)-5-[(benzyloxy)amino]-piperidine-2-carbonitrile (II). The compound of Formula (II) was prepared according to the process disclosed in WO2013038330. The compound of Formula (II) is converted to a compound of Formula (IV). In some embodiments, compound of Formula (II) is reacted with a suitable hydrolyzing agent in presence of a suitable solvent to obtain a compound of Formula (IV). Typical, non-limiting examples of a suitable hydrolyzing agent include trimethylsilyl chloride, hydrochloric acid, methanolic hydrogen chloride and the like. Typical, non-limiting examples of a suitable solvent include methanol, ethanol, tetrahydrofuran, ethylene dichloride, nitromethane or a mixture thereof. In some embodiments, compound of Formula (II) is hydrolyzed with trimethylsilyl chloride in presence of methanol to obtain a compound of Formula (IV). In some other embodiments, compound of Formula (II) is first hydrolyzed with hydrochloric acid to obtain a compound of Formula (III), followed by treatment with trimethylsilyl chloride to obtain a compound of Formula (IV). In some other embodiments, compound of Formula (III) is reacted with thionyl chloride in presence of methanol to obtain a compound of Formula (IV).

The compound of Formula (IV) is cyclized with a suitable reagent to obtain a compound of Formula (V). In some embodiments, a compound of Formula (IV) is reacted with a suitable cyclizing agent in presence of a suitable base and a suitable catalyst to obtain a compound of Formula (V). In some embodiments, a compound of Formula (IV) is reacted with triphosgene in presence of triethylamine and 4-dimethylaminopyridine to obtain a compound of Formula (V).

The compound of Formula (V) is hydrolyzed, followed by sodium salt formation to obtain a compound of Formula (I). The compound of Formula (V) is hydrolyzed in presence of a suitable hydrolyzing reagent and a suitable solvent. Typical, non-limiting examples of a suitable solvent include acetone-water mixture, tetrahydrofuran-water mixture, dioxane-water mixture and the like. In some embodiments, compound of Formula (V) is hydrolyzed in presence of lithium hydroxide and acetone-water mixture. The hydrolysis reaction is followed by sodium salt formation to obtain a compound of Formula (I). In some embodiments, the sodium salt formation is carried out by reacting with sodium-2-ethylhexanoate to obtain a compound of Formula (I). In some other embodiments, sodium salt formation is achieved by contacting with a suitable sodium exchange resin.

Scheme 1

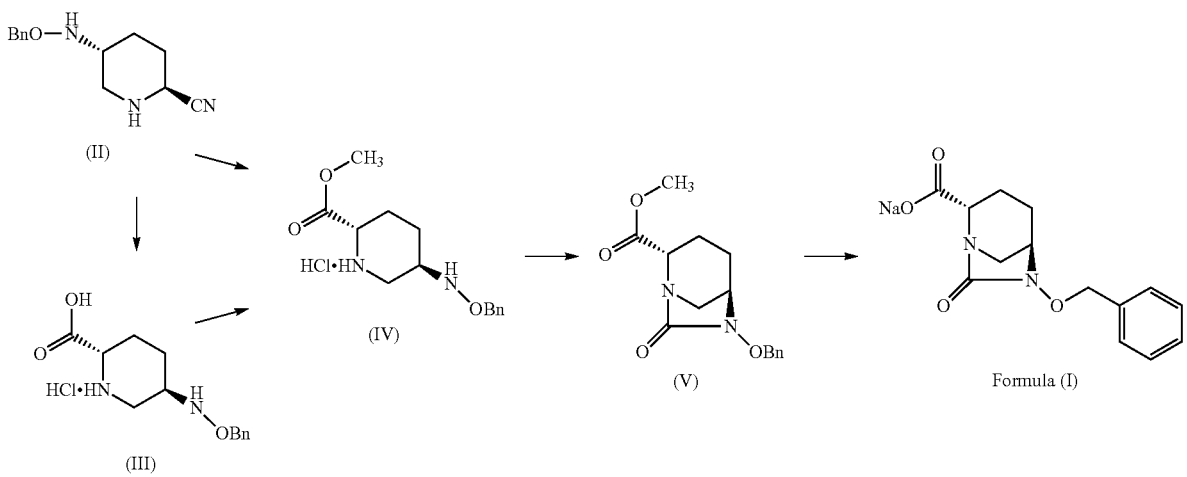

In some embodiments, there is provided a process for preparation of a compound of Formula (I), said process comprising:

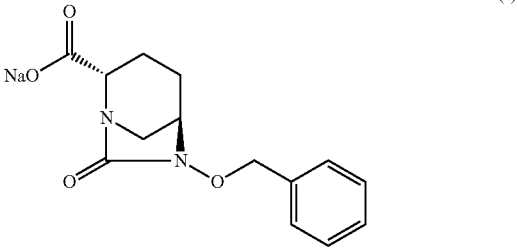

Formula (I)

(a) reacting a compound of Formula (II) with trimethylsilyl chloride in presence of methanol to obtain a compound of Formula (IV);

Formula (II)

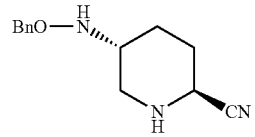

Formula (IV)

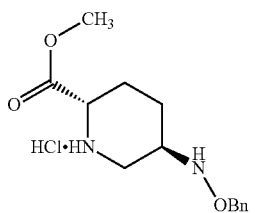

(b) cyclizing a compound of Formula (IV) in presence of triphosgene, triethylamine and 4-dimethylaminopyridine to obtain a compound of Formula (V); and Formula (V)

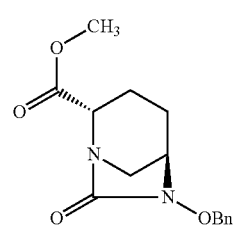

(c) treating a compound of Formula (V) with lithium hydroxide monohydrate, followed by sodium salt formation to obtain a compound of Formula (I).

In some embodiments, compound of Formula (I) is prepared using a process described in Scheme I.

In another general aspect, there is provide a process for preparation of a compound of Formula (I), said process comprising:

Formula (I)

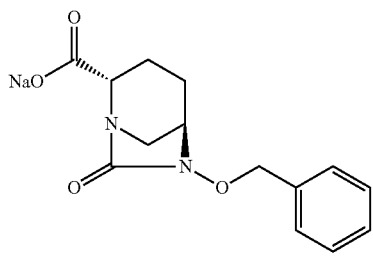

(a) hydrolysis of a compound of Formula (II) to obtain a compound of Formula (III);

Formula (II)

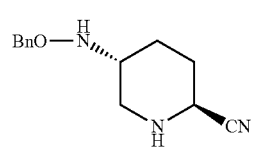

Formula (III)

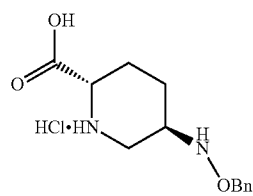

(b) reacting a compound of Formula (III) with di-tert-butyldicarbonate to obtain a compound of Formula (VI);

Formula (VI)

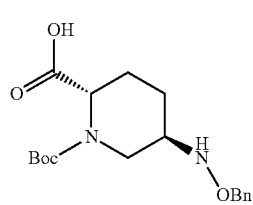

(c) reacting a compound of Formula (VI) with 4-methoxybenzyl alcohol to obtain a compound of Formula (VII);

Formula (VII)

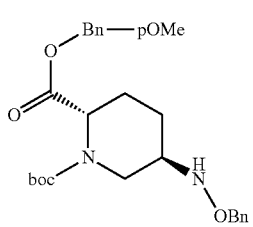

(d) hydrolysis of a compound of Formula (VII) to obtain a compound of Formula (VIII);

Formula (VIII)

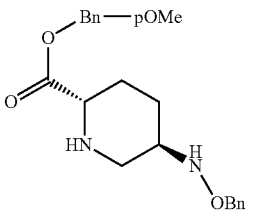

(e) cyclizing a compound of Formula (VIII) to obtain a compound of Formula (IX); and Formula (IX)

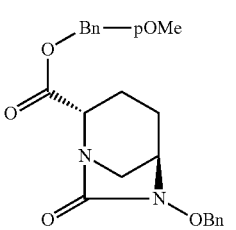

(f) converting a compound of Formula (IX) to a compound of Formula (I).

In some embodiments, a compound of Formula (I) is prepared by using a general procedure described in Scheme 2. Typically, a compound of Formula (II) is first converted to a compound of Formula (III). In some embodiments, a compound of Formula (II) is hydrolyzed with hydrochloric acid to obtain a compound of Formula (III). The compound of Formula (III) is then reacted with an amine protecting group to obtain a compound of Formula (VI). In some embodiments, compound of Formula (III) is reacted with di-tert-butyldicarbonate (Boc anhydride), in presence of a suitable base such as sodium hydroxide to obtain a compound of Formula (VI).

The hydroxyl group of a compound of Formula (VI) is protected with suitable reagent to obtain a compound of Formula (VII). In some embodiments, compound of Formula (VI) is reacted with 4-methoxybenzyl alcohol, in presence of a suitable carboxyl group activating agent and a suitable solvent to obtain a compound of Formula (VII). Typical, non-limiting examples of carboxyl group activating agent include EDC.HCl, HOBt, dicyclohexylcarbodiimide, carbonyldiimidazole or a mixture thereof. Typical, non-limiting examples of a suitable solvent include dimethylformamide, dimethylsulphoxide and a mixture thereof.

The compound of Formula (VII) is hydrolyzed to obtain a compound of Formula (VIII). In some embodiments, compound of Formula (VII) is hydrolyzed with hydrochloric acid to remove the amine protecting group and obtain a compound of Formula (VIII). The compound of Formula (VIII) is cyclized in presence of a suitable reagent, a suitable base and a suitable solvent to obtain compound of Formula (IX). Typical, non-limiting examples of a cyclizing reagent include triphosgene and the like. Typical, non-limiting examples of a suitable base include triethyl amine, N-ethyldiisopropylamine, N-methyl morpholine and the like. Typical, non-limiting examples of a suitable solvent include acetonitrile, dichloromethane or a mixture thereof. In some embodiments, compound of Formula (VIII) is reacted with triphosgene in presence of triethyl amine, 4-dimethylaminopyridine and acetonitrile to obtain a compound of Formula (IX).

The hydroxyl protecting group of a compound of Formula (IX) is removed by action of a suitable deprotecting agent. In some embodiments, compound of Formula (IX) is reacted with trifluroacetic acid to remove the 4-methoxybenzyl group. The deprotection of 4-methoxybenzyl group is followed with sodium salt formation to obtain compound of Formula (I). In some embodiments, the sodium salt formation is done by reacting with a suitable reagent such as sodium-2-ethyl hexanoate acetate to obtain a compound of Formula (I). In some other embodiments, sodium salt formation is achieved by contacting with a sodium exchange resin.

Scheme 2

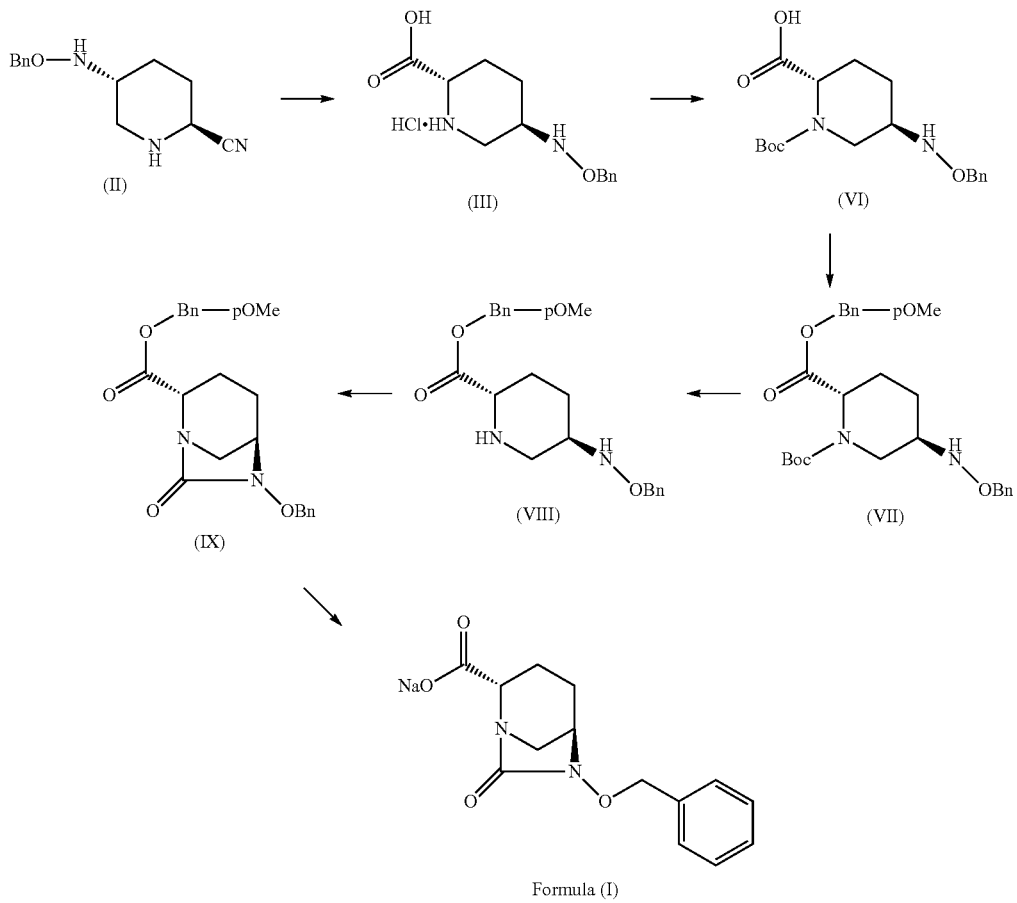

Formula (I)

In some embodiments, there is provided a process for preparation of a compound of Formula (I), said process comprising:

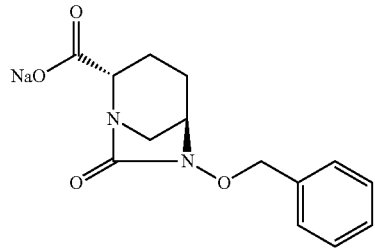
Formula (I)

(a) hydrolysis of a compound of Formula (II) in presence of hydrochloric acid to obtain a compound of Formula (III);

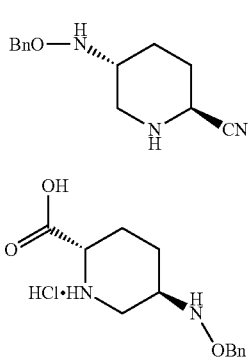

Formula (II)

Formula (III)

(b) reacting a compound of Formula (III) with di-tert-butyldicarbonate in presence of a base to obtain a compound of Formula (VI);

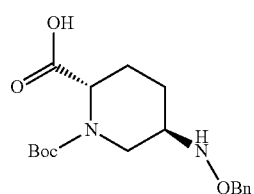
Formula (VI)

(c) reacting a compound of Formula (VI) with 4-methoxybenzyl alcohol in presence of 1-ethyl-3-(3-methylaminopropyl)carbodiimide hydrochloride and 1-hydroxy benzotriazole to obtain a compound of Formula (VII);

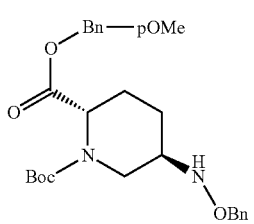
Formula (VII)

(d) hydrolysis of a compound of Formula (VII) in presence of hydrochloric acid to obtain a compound of Formula (VIII);

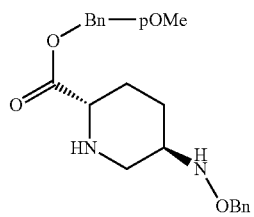
Formula (VIII)

(e) cyclizing a compound of Formula (VIII) in presence of triphosgene, triethylamine and 4-dimethylaminopyridine to obtain a compound of Formula (IX); and

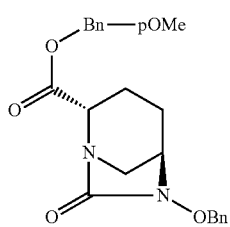
Formula (IX)

(f) treating a compound of Formula (IX) with trifluoroacetic acid, followed by sodium salt formation to obtain a compound of Formula (I).

In some embodiments, compound of Formula (I) is prepared using a process described in Scheme 2.

It will be readily apparent to one skilled in the art that varying substitutions and modifications may be made to the invention disclosed herein without departing from the scope and spirit of the invention. For example, those skilled in the art will recognize that the invention may be practiced using a variety of different compounds within the described generic descriptions.

EXAMPLES

The following examples illustrate the embodiments of the invention that are presently best known. However, it is to be understood that the following are only exemplary or illustrative of the application of the principles of the present invention. Numerous modifications and alternative compositions, methods, and systems may be devised by those skilled in the art without departing from the spirit and scope of the present invention. The appended claims are intended to cover such modifications and arrangements. Thus, while the present invention has been described above with particularity, the following examples provide further detail in connection with what are presently deemed to be the most practical and preferred embodiments of the invention.

Example 1

Synthesis of sodium (2S, 5R)-6-(benzyloxy)-7-oxo-1,6-diazabicyclo[3.2.1]octane-2-carboxylate

Step 1: Synthesis of hydrochloride salt of methyl (2S,5R)-5-[(benzyloxy)amino]piperidine-2-carboxylate (IV)

Method-I

To a solution of (2S, 5R)-5-[(benzyloxy)amino]-piperidine-2-carbonitrile (II) (200 mg, 0.865 mmol) in methanol (1 ml), trimethylsilyl chloride (0.440 ml, 3.5 mmol) was added slowly under stirring, at 25° C. After 2 hours, the mixture was heated to 55° C. and stirring continued further for 18 hours. The solvent was evaporated under reduced pressure and the residue was suspended in aqueous saturated solution of sodium bicarbonate (5 ml). The mixture was extracted with ethyl acetate (2×5 ml). The combined organic phase was dried over sodium sulphate and the solvent was evaporated under reduced pressure. The residue obtained was purified by column chromatography over silica-gel (60-120 mesh) and elution was done with mixture of ethyl acetate and hexane. The combined fractions were concentrated and stirred with ethereal hydrogen chloride solution to obtain 100 mg of hydrochloride salt of methyl (2S, 5R)-5-[(benzyloxy) amino]-piperidine-2-carboxylate hydrochloride(IV), in 41% yield.

Method-II

Step 1 (a): Preparation of hydrochloride salt of (2S, 5R)-5-[(benzyloxy)amino]-piperidine-2-carboxylic acid (III)

The aqueous solution of 6N hydrochloric acid (10 ml) was added to (2S,5R)-5-[(benzyloxy)amino]-piperidine-2-carbonitrile (II) (500 mg, 2.164 mmol) under stirring, and was heated to about 75-80° C. After 16 hours, the solvent was evaporated under reduced pressure and the residue was leached with ethyl acetate (5 ml) to obtain a solid product. The solid was dried under reduced pressure to obtain 610 mg of hydrochloride salt of (2S,5R)-5-[(benzyloxy)amino]-piperidine-2-carboxylic acid (III) in 98% yield. This solid was used as such, without further purification, in the next step.

Analysis:
Mass: 251 (M+1); for Molecular Weight: 250 and Molecular Formula: $C_{13}H_{18}N_2O_3 \cdot HCl$;
$^1H$ NMR (400 MHz, DMSO): δ 7.34-7.24 (m, 5H), 6.72-6.70 (d, 1H), 4.55 (s, 2H), 3.21-3.17 (m, 2H), 3.06-2.99 (dd, 2H), 2.10-2.06 (dd, 1H), 1.80-1.77 (d, 1H), 1.44-1.22 (m, 2H).

Step 1 (b): Preparation of hydrochloride salt of methyl (2S, 5R)-5-[(benzyloxy)amino]-piperidine-2-carboxylate hydrochloride (IV)

Methanol (5 ml) was added to a stirred mixture of hydrochloride salt of (2S,5R)-5-(benzyloxyamino) piperidine-2-carboxylic acid (III) (500 mg, 2 mol) and trimethyl chlorosilane (1 ml) at room temperature. After 26 hour, the solvent was evaporated under reduced pressure to obtain a solid residue. The solid residue was dried under reduced pressure to obtain 522 mg of hydrochloride salt of methyl (2S, 5R)-5-[(benzyloxy)amino]-piperidine-2-carboxylate (IV) as a white solid, in 98% yield. The solid was used without purification for the next step.

Analysis:
Mass: 265 (M+1) as free acid; for Molecular Weight: 300.5 and Molecular Formula: $C_{14}H_{20}O_3 \cdot HCl$.

Step 2: Preparation of methyl (2S, 5R)-6-(benzyloxy)-7-oxo-1,6-diaza-bicyclo[3.2.1] octane-2-carboxylate (V)

To a stirred solution of hydrochloride salt of methyl (2S,5R)-methyl-5-[(benzyloxy)amino]-piperidine-2-carboxlyate (IV) (300 mg, 1.0 mol) in acetonitrile (4.5 ml) at 0° C., triethylamine (0.696 ml, 5 mol) was added, followed by addition of a solution of triphosgene (130 mg, 0.44 mol) in acetonitrile (1.3 ml). After five minutes, DMAP (12.2 mg, 0.1 mol) was added and the mixture was allowed to warm to room temperature (25° C.). After stirring for a period of 5 hours, an aqueous saturated sodium hydrogen carbonate solution (5 ml) was added. The solvent was evaporated under reduced pressure and the aqueous layer extracted with dichloromethane (2×5 ml). The combined organic layer was washed with water (5 ml), with brine (5 ml), dried over anhydrous sodium sulphate and evaporated under reduced pressure to obtain a thick residue. The crude product was purified by silica gel (60-120 mesh) column chromatography using mixture of ethyl acetate and hexane as an eluent. The evaporation of combined fractions gave 143 mg of methyl (2S, 5R)-6-(benzyloxy)-7-oxo-1,6-diaza-bicyclo[3.2.1]octane-2-carboxylate (V) in 49% yield.

Analysis:
Mass: 291 (M+1); for Molecular Weight: 290 and Molecular Formula: $C_{15}H_{18}N_2O_4$;
$^1H$ NMR (400 MHz, $CDCl_3$): δ 7.43-7.25 (m, 5H), 5.06-5.03 (d, 1H), 4.91-4.88 (d, 1H), 4.12-4.10 (m, 1H), 3.77 (s, 3H), 3.32 (s, 1H), 3.07-3.04 (s, 1H), 2.92-2.89 (s, 1H), 2.12-2.01 (m, 3H), 1.70-1.62 (m, 1H).

Step 3: Preparation of sodium (2S, 5R)-6-(benzyloxy)-7-oxo-1,6-diazabicyclo[3.2.1]octane-2-carboxylate (I)

A solution of lithium hydroxide monohydrate (23 mg, 0.548 mmol) in a mixture of acetone: water (0.43 ml: 1.38 ml) was added to a stirred solution of a compound of Formula (V) (100 mg, 0.344 mmol) in tetrahydrofuran (1 ml), at about −10 to 0° C. After 2 hours the pH of the solution was adjusted to 8-8.5 by addition of a aqueous solution of 2N hydrochloric acid. The reaction mixture was extracted with ethyl acetate (2 ml). The aqueous layer was acidified to pH 2-2.5 by addition of a aqueous solution of 2N hydrochloric acid. The mixture was extracted with dichloromethane (2 ml). The organic layer was concentrated under reduced pressure. The residue was dried at 4 mm Hg for 0.5 hour. The residue was diluted with 1 ml of acetone and to the clear solution was added sodium 2-ethylhexanoate (114 mg) in acetone (0.5 ml). The solution was stirred at room temperature for 24 hours. The separated precipitate was filtered under suction and the solid washed with additional acetone (1 ml). The solid was dried under reduced pressure to obtain 70 mg of sodium (2S, 5R)-6-(benzyloxy)-7-oxo-1,6-diazabicyclo[3.2.1]octane-2-carboxylate (I) as an off-white solid in 68% yield.

Analysis:
Mass: 277 (M+1) as free acid; for Molecular Weight: 298 and Molecular Formula: $C_{14}H_{15}N_2O_4Na$;

¹H NMR (400 MHz, DMSO): δ 7.42-7.32 (m, 5H), 4.92-4.83 (q, 2H), 3.47 (s, 1H), 3.32-3.26 (m, 2H), 2.71-2.68 (m, 1H), 2.07-2.02 (m, 1H), 1.76-1.54 (m, 3H).

Example 2

Synthesis of sodium (2S, 5R)-6-(benzyloxy)-7-oxo-1,6-diazabicyclo[3.2.1]octane-2-carboxylate Step 1: Preparation of hydrochloride salt of (2S, 5R)-5-[(benzyloxy)amino]-piperidine-2-carboxylic acid (III)

Hydrochloride salt of (2S,5R)-5-[(benzyloxy)amino]-piperidine-2-carboxylic acid (III) is prepared as per procedure disclosed in Step 1 (a) of Example 1.

Step 2: Preparation of (2S,5R)-1-[(1,1-dimethylethyl)carbonyl]-5-[(benzyloxy)amino]-piperidine-2-carboxylic acid (VI)

To a stirred solution of hydrochloride salt of (2S, 5R)-5-[(benzyloxy)amino]-piperidine-2-carboxylic acid (III) (1 g, 0.034 mol) in 1,4-dioxane (5 ml) was added 2N aqueous sodium hydroxide solution (0.480 g, 0.012 mol) at about 0° C. After 5 minutes of the stirring, boc anhydride (1.0 ml, 0.00435 mol) was added. The reaction mixture was allowed to warm to 25° C. and stirring was continued further for 16 hours. The solvent was evaporated under reduced pressure and the pH of the residual mass was adjusted to pH 2.0 by using 30% potassium hydrogen sulphate at about 0° C. The mixture was extracted with ethyl acetate (2×10 ml). The organic layer was washed with water (5 ml), brine (5 ml), dried over anhydrous sodium sulphate and concentrated under reduced pressure to obtain 868 mg of (2S,5R)-1-[(1,1-dimethylethyl)carbonyl]-5-[(benzyloxy)amino]-piperidine-2-carboxylic acid (VI) in 62% yield.

Analysis:
Mass: 351 (M+1); for Molecular Weight: 350 and Molecular Formula: $C_{18}H_{26}N_2O_5$;
¹H NMR (400 MHz, DMSO): δ 7.34-7.24 (m, 5H), 4.63 (br s, 2H), 4.02-3.98 (d, 2H), 3.07-2.94 (m, 2H), 1.88 (br s, 2H), 1.76-1.57 (m, 2H), 1.34 (s, 9H).

Step 3: Synthesis of (2S,5R)-2-[(4-methoxyphenyl)methyl]-1-(1,1-dimethylethyl)-5-[(benzyloxy)amino]-piperidine-1,2-dicarboxylate To a stirred solution of (2S,5R)-1-[(1,1-dimethylethyl)carbonyl]-5-[(benzyloxy)amino]-piperidine-2-carboxylic acid (VI) (5 g, 0.0142 mol) in dimethylformamide (50 ml), at about 0° C., were added successively EDC.HCl (4.1 g, 0.021 mol), HOBt (2.2 g, 0.0143 mol), N-methyl morpholine (4.7 ml, 0.0426 mol) and 4-methoxy benzyl alcohol (4.7 ml, 0.0426 mol). The reaction mixture was allowed to warm to 25° C. and the stirring continued further. After 16 hours, the resulting mixture was slowly poured into chilled water (250 ml) under stirring and extracted with ethyl acetate (2×100 ml). The organic layer was separated, washed with water (50 ml), brine (50 ml), dried over anhydrous sodium sulphate and the solvent evaporated under reduced pressure. The residue thus obtained was purified by column chromatography over silica gel (60-120 mesh). The elution was done with a mixture of ethyl acetate and hexane. The combined fractions were concentrated to obtain 3.8 g of (2S,5R)-2-[(4-methoxyphenyl)methyl]-1-(1,1-dimethylethyl)-5-[(benzyloxy)amino]-piperidine-1,2-dicarboxylate (VII) as a white solid in 57% yield.

Analysis:
Mass: 471 (M+1); for Molecular Weight: 470 and Molecular Formula: $C_{26}H_{34}N_2O_6$;
¹H NMR (400 MHz, CDCl₃): δ 7.34-7.25 (m, 7H), 6.90-6.85 (m, 2H), 5.45 (s, 1H), 5.14-5.06 (m, 2H), 4.90 (s, 1H), 4.74-4.61 (m, 2H), 4.16-4.09 (br s, 1H), 3.82 (s, 3H), 3.12 (br m, 2H), 1.94 (br s, 2H), 1.66-1.49 (m, 2H), 1.42 (s, 9H).

Step 4: Synthesis of (2S, 5R)-2-(4-methoxypheny)methyl)-5-[(benzyloxy)amino]-piperidine-2-carboxylate (VIII)

To a stirred solution of (2S,5R)-2-[(4-methoxyphenyl)methyl]-1-(1,1-dimethylethyl)-5-[(benzyloxy)amino]-piperidine −1,2-dicarboxylate (VII) (500 mg, 1.06 mol) in tetrahydrofuran (5 ml), was added a cooled solution of 4N hydrochloric acid (3 ml) at 0° C. The reaction mixture was allowed to warm to 25° C. After 24 hours, tetrahydrofuran was distilled out under reduced pressure and the aqueous layer was extracted with ethyl acetate (2×5 ml). The combined organic layer was washed with water (5 ml), brine (5 ml), dried over anhydrous sodium sulphate and concentrated under reduced pressure to obtain a crude product. The crude product was purified by column chromatography over silica gel (60-120 mesh) using mixture of ethyl acetate and hexane as an eluent. The combined fractions were concentrated to obtain 110 mg of (2S, 5R)-2-(4-methoxypheny)methyl)-5-[(benzyloxy)amino]-piperidine-2-carboxylate (VIII) in 28% yield.

Analysis:
Mass: 371 (M+1) for Molecular Weight: 370 and Molecular Formula: $C_{21}H_{26}N_2O_4$;
¹H NMR (400 MHz, CDCl₃): δ 7.35-7.25 (m, 7H), 6.90-6.86 (m, 2H), 5.12 (m, 2H), 4.66 (s, 2H), 3.80 (s, 3H), 3.37-3.29 (m, 2H), 3.01-2.96 (m, 1H), 2.46-2.41 (m, 1H), 2.09-2.05 (m, 1H), 1.93-1.90 (m, 1H), 1.55-1.52 (m, 2H), 1.30-1.23 (m, 1H).

Step 5: Synthesis of (2S,5R)-2-[(4-methoxyphenyl)methyl]-6-(benzyloxy)-7-oxo-1,6-diaza-bicyclo [3.2.1]octane-2-carboxylate (IX)

To a stirred solution of (2S,5R)-2-(4-methoxypheny)methyl)-5-[(benzyloxy)amino]-piperidine-2-carboxylate (100 mg, 0.270 mol) in acetonitrile (1.5 ml) containing triethylamine (0.113 ml, 0.812 mol), was added solution of triphosgene (35 mg, 0.117 mol) in acetonitrile (0.350 ml), at 0° C. After five minutes, DMAP (4 mg, 0.0327 mol) was added and the reaction mixture was allowed to warm to 25° C. After 6 hours of stirring, a saturated solution of sodium hydrogen carbonate (5 ml) was added and acetonitrile was distilled out under reduced pressure. The aqueous layer was extracted with dichloromethane (2×5 ml). The combined organic layer was washed with water (5 ml), brine (5 ml), dried over anhydrous sodium sulphate and concentrated under reduced pressure. The residue was purified by column chromatography over silica gel (60-120 mesh) using mixtures of ethyl acetate and hexane as eluent. The combined fractions were evaporated to obtain 53 mg of (2S,5R)-2-[(4-methoxyphenyl)methyl]-6-(benzyloxy)-7-oxo-1,6-diaza-bicyclo [3.2.1]octane-2-carboxylate (IX) in 49% yield.

Analysis:
Mass: 397 (M+1); for Molecular Weight: 396 and Molecular Formula: $C_{12}H_{24}N_2O_5$;

¹H NMR (400 MHz, CDCl₃): δ 7.41-7.28 (m, 7H), 6.87-6.85 (m, 2H), 5.17 (m, 2H), 5.05-5.02 (d, 1H), 4.90-4.87 (d, 1H), 4.14-4.11 (s, 1H), 3.79 (s, 3H), 3.27 (s, 1H), 2.98-2.85 (d, 1H), 2.85-2.82 (d, 1H), 2.11-1.99 (m, 2H), 1.65-1.58 (m, 1H), 1.29-1.21 (m, 1H).

Step 6: Preparation of sodium (2S,5R)-6-(benzyloxy)-7-oxo-1,6-diazabicyclo [3.2.1]octane-2-carboxylate (I)

To a stirred solution of (2S,5R)-2-[(4-methoxyphenyl)methyl]-6-(benzyloxy)-7-oxo-1,6-diaza-bicyclo[3.2.1]octane-2-carboxylate (IX) (500 mg, 1.35 mol), in dichloromethane (5 ml) at 0° C., anisole (1 ml) and trifluoroacetic acid (2.5 ml) were added successively. The reaction mixture was allowed to warm to room temperature and stirring continued further for 17 hours. To the resulting reaction mixture was added hexane (100 ml) slowly, under stirring. After 10 minutes of stirring the hexane was decanted and the procedure repeated again with additional hexane (50 ml). The resulting oily residue was dried under reduced pressure (4 mm Hg) and co-evaporated with acetone (2×10 ml). To the residual concentrate, acetone (5 ml) was added to obtain a clear solution. To the obtained clear solution was added a solution of sodium 2-ethylhexanoate (450 mg) in acetone (2.5 ml) under stirring. After stirring for 66 hours, at about 25° C., the obtained precipitate was filtered, washed with acetone (2×5 ml), and dried on rotavapour at 40° C. for 3 hours to obtain 161 mg of sodium (2S,5R)-6-(benzyloxy)-7-oxo-1,6-diazabicyclo [3.2.1]octane-2-carboxylate (I) as white solid in 40% yield.

Analysis:

Mass: 277 (M+1) as free acid; for Molecular Weight: 298 and Molecular Formula: C₁₄H₁₅N₂O₄Na;

¹H NMR (400 MHz, DMSO): δ 7.42-7.32 (m, 5H), 4.92-4.83 (q, 2H), 3.47 (s, 1H), 3.32-3.26 (m, 2H), 2.71-2.68 (m, 1H), 2.07-2.02 (m, 1H), 1.76-1.54 (m, 3H).

The invention claimed is:

1. A process for preparation of a compound of Formula (I)

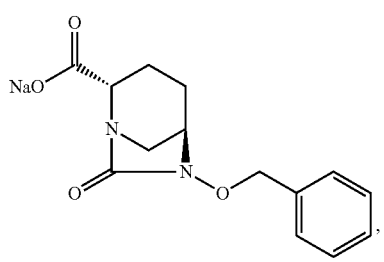

Formula (I)

wherein said process comprising:
(a) converting a compound of Formula (II) to a compound of Formula (IV);

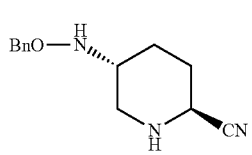

Formula (II)

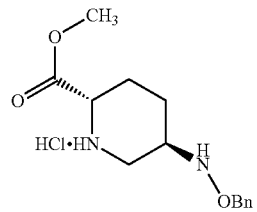

Formula (IV)

(b) cyclizing the compound of Formula (IV) to obtain a compound of Formula (V)

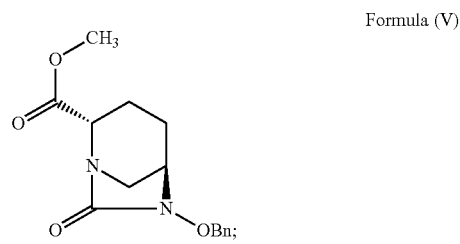 [SMILES: COC(=O)[C@@H]1CC[C@@H]2CN1C(=O)N2OCc1ccccc1]

Formula (V)

and
(c) converting the compound of Formula (V) to the compound of Formula (I).

2. The process according to claim 1, wherein the compound of Formula (IV) is obtained by treating the compound of Formula (II) with trimethylsilyl chloride in presence of methanol.

3. The process according to claim 1, wherein the compound of Formula (IV) is obtained by converting the compound of Formula (II) to a compound of Formula (III)

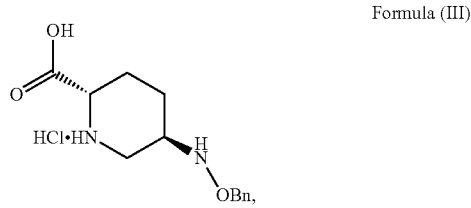

Formula (III)

followed by treatment with trimethylsilyl chloride.

4. The process according to claim 3, wherein the compound of Formula (II) is converted to the compound of Formula (III) in presence of hydrochloric acid.

5. A process for preparation of a compound of Formula (I)

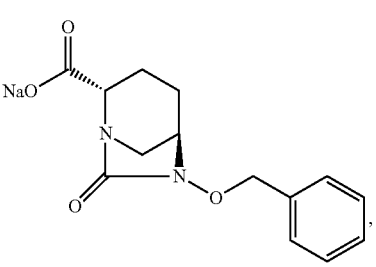

Formula (I)

wherein said process comprising:
(a) hydrolysis of a compound of Formula (II) to obtain a compound of Formula (III);

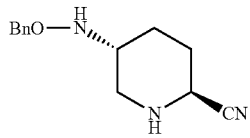
Formula (II)

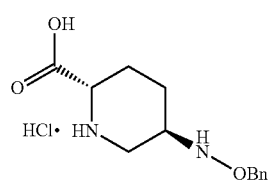
Formula (III)

(b) reacting the compound of Formula (III) with di-tert-butyldicarbonate to obtain a compound of Formula (VI)

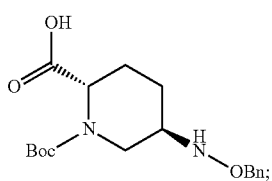
Formula (VI)

(c) reacting the compound of Formula (VI) with 4-methoxybenzyl alcohol to obtain a compound of Formula (VII)

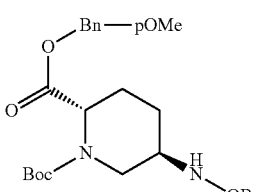
Formula (VII)

(d) hydrolysis of the compound of Formula (VII) to obtain a compound of Formula (VIII)

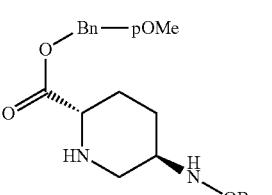
Formula (VIII)

(e) cyclizing the compound of Formula (VIII) to obtain a compound of Formula (IX)

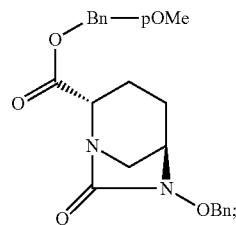
Formula (IX)

and
(f) converting the compound of Formula (IX) to the compound of Formula (I).

6. The process according to claim 5, wherein the compound of Formula (VII) is obtained by reacting the compound of Formula (VI) with 4-methoxybenzyl alcohol in presence of a carboxylic group activating agent.

7. The process according to claim 6, wherein the carboxylic group activating agent is selected from the group consisting of 1-ethyl-3-(3-methylaminopropyl)carbodiimide hydrochloride, 1-hydroxy benzotriazole, dicyclohexylcarbodiimide, carbonyldiimidazole; and a mixture thereof.

8. The process according to claim 5, wherein cyclization is carried out in presence of triphosgene, triethylamine and 4-dimethylaminopyridine.

9. The process for preparation of the compound of Formula (I)

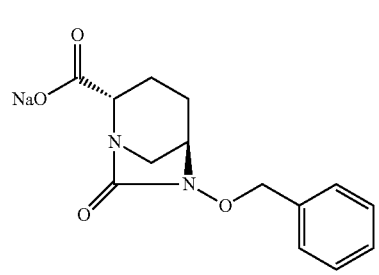
Formula (I)

according to claim 1, wherein said process comprising:
(a) reacting the compound of Formula (II) with trimethylsilyl chloride in presence of methanol to obtain the compound of Formula (IV);

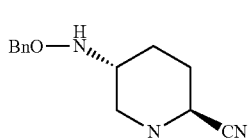
Formula (II)

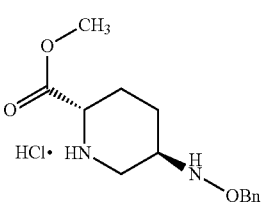
Formula (IV)

(b) cyclizing the compound of Formula (IV) in presence of triphosgene, triethylamine and 4-dimethylaminopyridine to obtain the compound of Formula (V)

Formula (V)

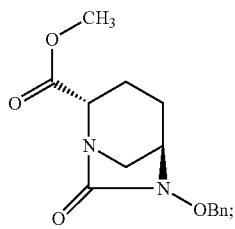

and (c) treating the compound of Formula (V) with lithium hydroxide monohydrate, followed by sodium salt formation to obtain the compound of Formula (I).

10. The process for preparation of the compound of Formula (I)

Formula (I)

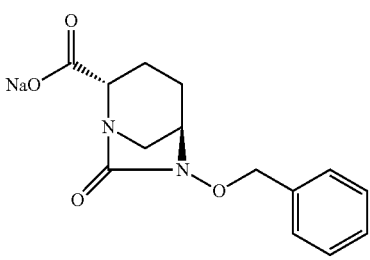

according to claim 5, wherein said process comprising:
(a) hydrolysis of the compound of Formula (II) in presence of hydrochloric acid to obtain the compound of Formula (III);

Formula (II)

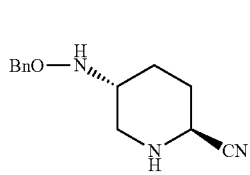

Formula (III)

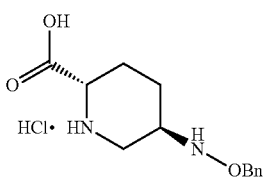

(b) reacting the compound of Formula (III) with di-tert-butyldicarbonate in presence of a base to obtain the compound of Formula (VI)

Formula (VI)

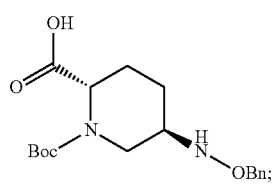

(c) reacting the compound of Formula (VI) with 4-methoxybenzyl alcohol in presence of 1-ethyl-3-(3-methylaminopropyl)carbodiimide hydrochloride and 1-hydroxy benzotriazole to obtain the compound of Formula (VII)

Formula (VII)

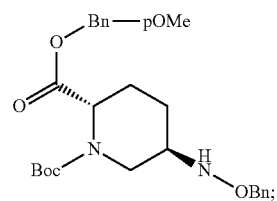

(d) hydrolysis of the compound of Formula (VII) in presence of hydrochloric acid to obtain the compound of Formula (VIII)

Formula (VIII)

(e) cyclizing the compound of Formula (VIII) in presence of triphosgene, triethylamine and 4-dimethylaminopyridine to obtain the compound of Formula (IX)

Formula (IX)

and (f) treating the compound of Formula (IX) with trifluoroacetic acid, followed by sodium salt formation, to obtain the compound of Formula (I).

11. The process according to claim 1, wherein cyclization is carried out in presence of triphosgene, triethylamine and 4-dimethylaminopyridine.

* * * * *